United States Patent [19]

Nakane et al.

[11] Patent Number: 4,734,425
[45] Date of Patent: Mar. 29, 1988

[54] 7-OXABICYCLOHEPTANE SUBSTITUTED HYDROXAMIC ACID PROSTAGLANDIN ANALOGS

[75] Inventors: Masami Nakane, Aichi, Japan; Joyce Reid, Dayton, N.J.

[73] Assignee: E. R. Squibb & Sons, Inc., Princeton, N.J.

[21] Appl. No.: 920,006

[22] Filed: Oct. 17, 1986

[51] Int. Cl.⁴ .................. C07D 307/00; C07D 405/06; A61K 31/34; A61K 31/41
[52] U.S. Cl. ................................. 514/382; 514/469; 548/253; 549/463
[58] Field of Search ............... 514/382, 469; 548/253; 549/463

[56] References Cited

U.S. PATENT DOCUMENTS

| | | | |
|---|---|---|---|
| 4,143,054 | 3/1979 | Sprague | 260/346.22 |
| 4,187,236 | 2/1980 | Sprague | 260/346.22 |
| 4,220,594 | 9/1980 | Sprague | 260/345.9 |
| 4,228,180 | 10/1980 | Sprague | 424/285 |
| 4,254,044 | 3/1981 | Sprague | 260/347.8 |
| 4,416,896 | 11/1983 | Nakane et al. | 424/285 |
| 4,456,615 | 6/1984 | Nakane et al. | 424/285 |
| 4,456,617 | 6/1984 | Nakane et al. | 424/285 |
| 4,607,048 | 8/1986 | Nakane | 514/469 |
| 4,638,012 | 1/1987 | Nakane | 514/469 |

FOREIGN PATENT DOCUMENTS 0043292 8/1982 European Pat. Off. .
0082646 6/1983 European Pat. Off. .
2039909 8/1980 United Kingdom .

Primary Examiner—Robert Gerstl
Attorney, Agent, or Firm—Lawrence S. Levinson; Burton Rodney

[57] ABSTRACT

7-Oxabicycloheptane substituted hydroxamic acid prostaglandin analogs are provided having the structural formula

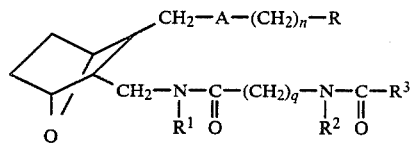

wherein A is —CH=CH— or —CH$_2$-CH$_2$—; n is 1 to 5; R is CO$_2$H, CO$_2$alkyl, CO$_2$alkali metal, CO$_2$polyhydroxyamine salt, —CH$_2$OH,

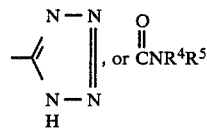 , or $CNR^4R^5$ wherein $R^4$ and $R^5$ are the same or different and are H, lower alkyl, hydroxy, lower alkoxy or aryl, at least one of $R^4$ and $R^5$ being other than hydroxy and lower alkoxy; q is 1 to 12, $R^1$ is H or OH; $R^2$ is OH or H, provided that one of $R^1$ and $R^2$ is OH and the other is H; and $R^3$ is H, lower alkyl, lower alkenyl, lower alkynyl, aryl, arylalkyl, lower alkoxy, aryloxy, arylalkyloxy, amino, alkylamino arylamino, arylalkylamino,

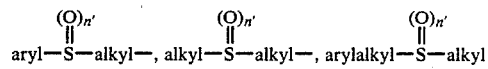

(wherein n' is 0, 1 or 2), alkylaminoalkyl, arylaminoalkyl, arylalkylaminoalkyl, alkoxyalkyl, aryloxyalkyl or arylalkoxyalkyl.

The compounds are cardiovascular agents useful, for example, in the treatment of thrombotic disease.

13 Claims, No Drawings

7-OXABICYCLOHEPTANE SUBSTITUTED HYDROXAMIC ACID PROSTAGLANDIN ANALOGS

DESCRIPTION OF THE INVENTION

The present invention relates to 7-oxabicycloheptane substituted hydroxamic acid prostaglandin analogs which are cardiovascular agents useful, for example, in the treatment of thrombotic disease. These compounds have the structural formula

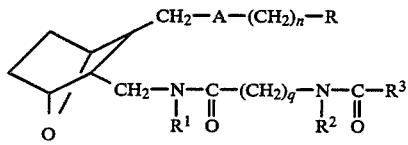

including all stereoisomers thereof, wherein A is —CH=CH— or —CH$_2$—CH$_2$—; n is 1 to 5; R is CO$_2$H, CO$_2$alkyl, CO$_2$ alkali metal, CO$_2$polyhydroxyamine salt, —CH$_2$OH,

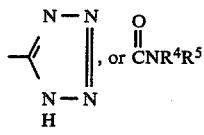

wherein $R^4$ and $R^5$ are the same or different and are H, lower alkyl, hydroxy, lower alkoxy or aryl, at least one of $R^4$ and $R^5$ being other than hydroxy and lower alkoxy; $R^1$ is H or OH; $R^2$ is OH or H, provided that one of $R^1$ and $R^2$ is OH and the other is H, q is 1 to 12; and $R^3$ is H, lower alkyl, lower alkenyl, lower alkynyl, aryl, arylalkyl, lower alkoxy, arylalkyloxy, aryloxy, alkylamino, arylalkylamino, arylamino, lower alkyl-S-, aryl-S-, arylalkyl-S-,

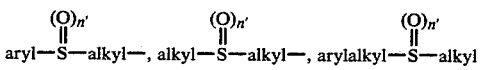

(wherein n' is 0, 1 or 2), alkylaminoalkyl, arylaminoalkyl, arylalkylaminoalkyl, alkoxyalkyl, aryloxyalkyl or arylalkoxyalkyl.

The term "lower alkyl" or "alkyl" as employed herein alone or as part of another group includes both straight and branched chain carbons, containing 1 to 12 carbons in the normal chain, preferably 1 to 7 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or CF$_3$, an alkoxy substituent, an aryl substituent, an alkyl-aryl substituent, a haloaryl substituent, a cycloalkyl substituent, an alkylcycloalkyl substituent, hydroxy, and alkylamino substituent, an alkanoylamino substituent, an arylcarbonylamino substituent, a nitro substituent, a cyano substituent, a thiol substituent or an alkylthio substituent.

The term "cycloalkyl" as employed herein alone or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups, 1 or 2 lower alkoxy groups, 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups, and/or 1 or 2 alkylthio groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, halogens (Cl, Br or F), 1 or 2 lower alkoxy groups, 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups, and/or 1 or 2 alkylthio groups.

The term "aralkyl", "aryl-alkyl" or "aryl-lower alkyl" as used herein alone or as part of another group refers to lower alkyl groups as discussed above having an aryl substituent, such as benzyl.

The term "lower alkoxy", "alkoxy", or "aryloxy" or "aralkoxy" as employed herein alone or as part of another group includes any of the above lower alkyl, alkyl, aralkyl or aryl groups linked to an oxygen atom.

The term "lower alkylthio", "alkylthio", "arylthio" or "aralkylthio" as employed herein alone or as part of another group includes any of the above lower alkyl, alkyl, aralkyl or aryl groups linked to a sulfur atom.

The term "lower alkylamino", "alkylamino", "arylamino", "arylalkylamino" as employed herein alone or as part of another group includes any of the above lower alkyl, alkyl, aryl or arylalkyl groups linked to a nitrogen atom.

The term "alkanoyl" as used herein as part of another group refers to lower alkyl linked to a carbonyl group.

The term "lower alkenyl" as used herein by itself or as part of another group refers to straight or branched chain radicals of 2 to 12 carbons, preferably 2 to 6 carbons in the normal chain, which include one double bond in the normal chain, such as 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl and the like.

The term "lower alkynyl" as used herein by itself or as part of another group refers to straight or branched chain radicals of 2 to 12 carbons, preferably 2 to 6 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like.

The term (CH$_2$)$_n$ includes straight or branched chain radicals having from 1 to 5 carbons in the normal chain and may contain one or more lower alkyl and/or halogen substituents. Examples of (CH$_2$)$_n$ groups include

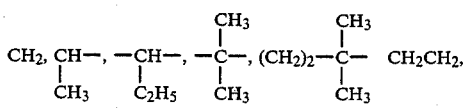

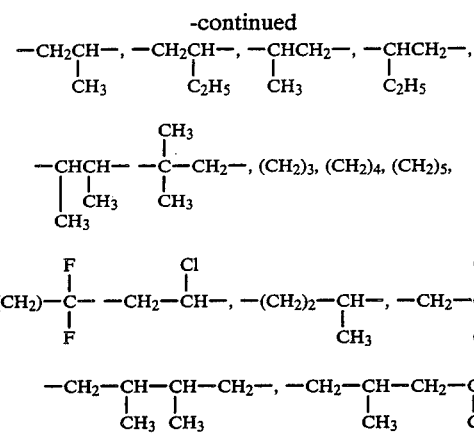

and the like.

The term $(CH_2)_q$ includes straight or branched chain radicals having from 1 to 12 carbons in the normal chain and includes any of the above examples of $(CH_2)_n$ groups as well as $(CH_2)_6$, $(CH_2)_7$, $(CH_2)_8$, $(CH_2)_9$, $(CH_2)_{10}$, $(CH_2)_{11}$, $(CH_2)_{12}$, and may be unsubstituted or substituted by one or more halo, hydroxy, alkoxy, amine, alkylamine, arylamine, amide, thioamide, thiol, alkylthio, arylthio, cyano or nitro groups.

The term "amide" refers to the group

wherein $R^6$ and $R^7$ are independently hydrogen, lower alkyl or aryl.

The term "polyhydroxyamine salt" refers to glucamine salt or tris(hydroxymethyl)aminomethane.

The term "halogen" or "halo" as used herein refers to chlorine, bromine, fluorine, iodine and $CF_3$, with chlorine or fluorine being preferred.

Preferred are those compounds of formula I wherein A is a $-CH=CH-$, n is 1 or 4, R is $CO_2H$ or $CH_2OH$; $R^1$ is H or OH and $R^2$ is OH or H; $(CH_2)_q$ is $-CH_2-$; $R^2$ is H or $CH_3$, and $R^3$ is lower alkyl, such as pentyl, hexyl, or heptyl or lower alkoxy, such as pentoxy, lower alkylamino such as pentylamino or arylthioalkyl, such as phenylthiomethyl.

The compounds of formula I of the invention may be prepared as described below.

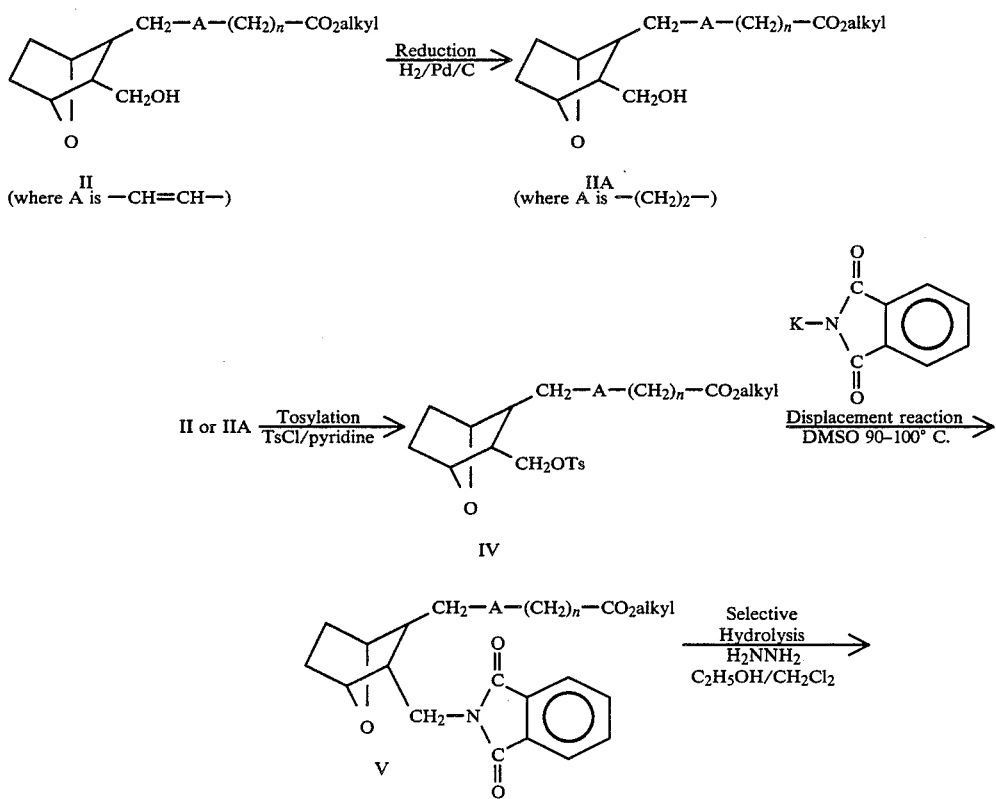

-continued
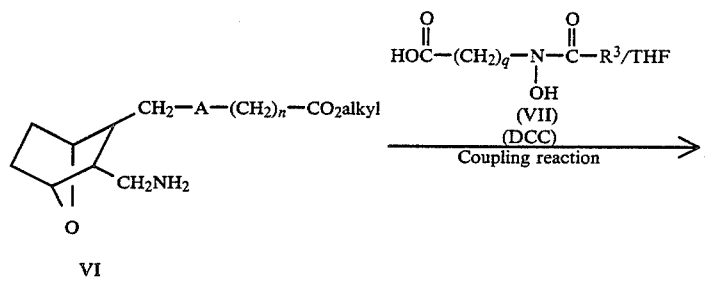
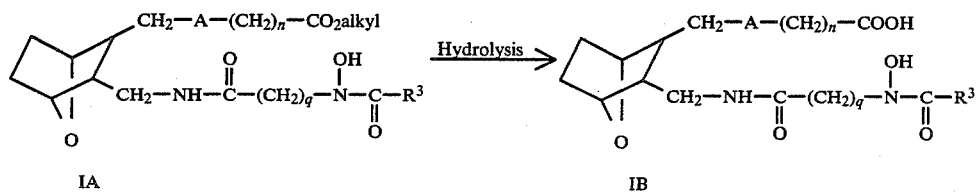
B. Preparation of starting material VII
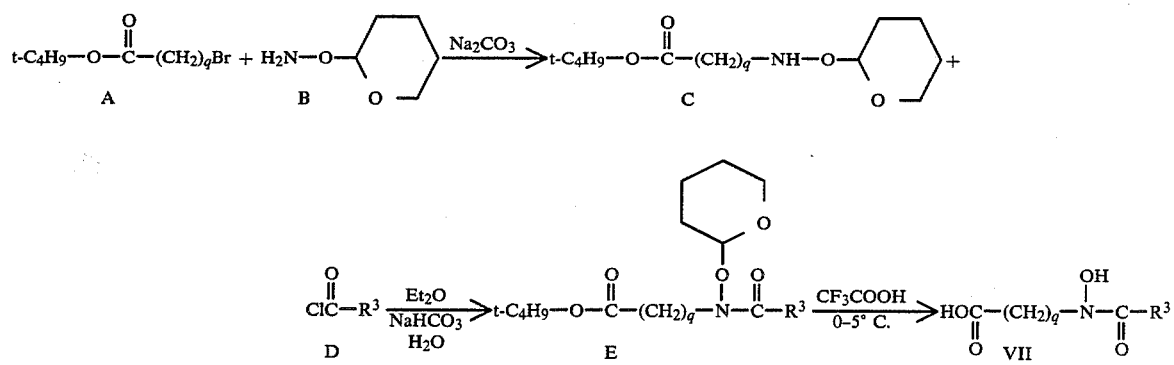
C. Where $R^1$ is OH and $R^2$ is H
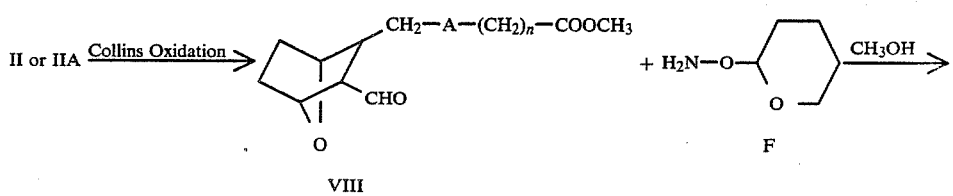
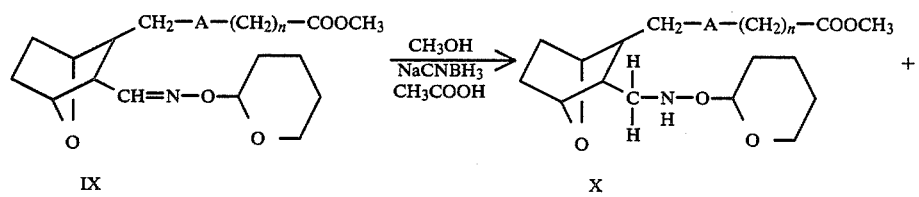
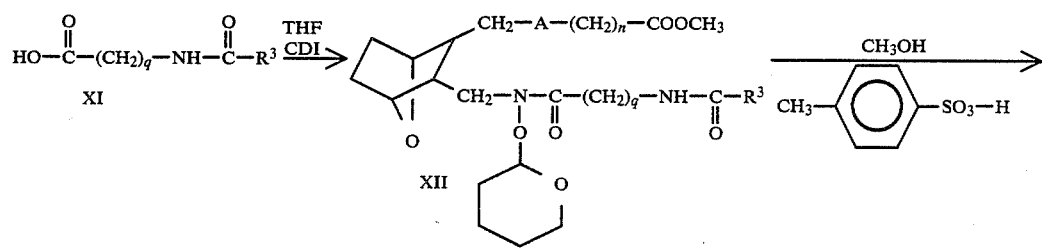

-continued

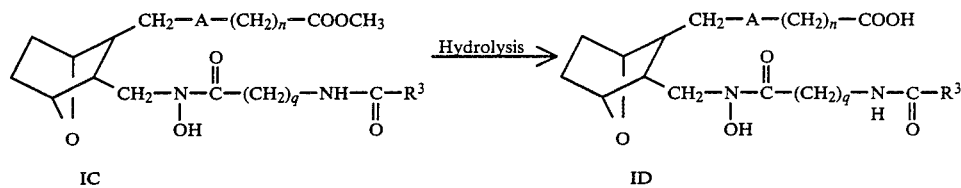

IC →Hydrolysis→ ID

D. Where R is $\overset{O}{\underset{\|}{C}}NR^4R^5$ (wherein $R^4$ and $R^5$ are other than hydroxy or alkoxy)

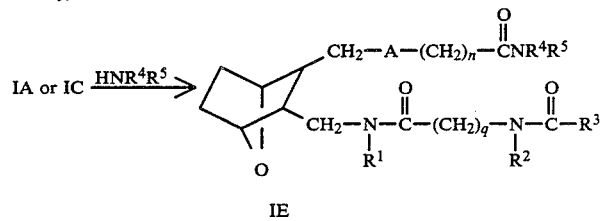

IA or IC →$HNR^4R^5$→ IE

E. Where R is $-\!\!\!\!\begin{array}{c}N\!=\!N\\ \diagup\phantom{xx}\|\\ \phantom{xx}\diagdown\\ N\!-\!N\\ \phantom{xx}H\end{array}$ , A is CH=CH, $R^1$ is H and $R^2$ is OH

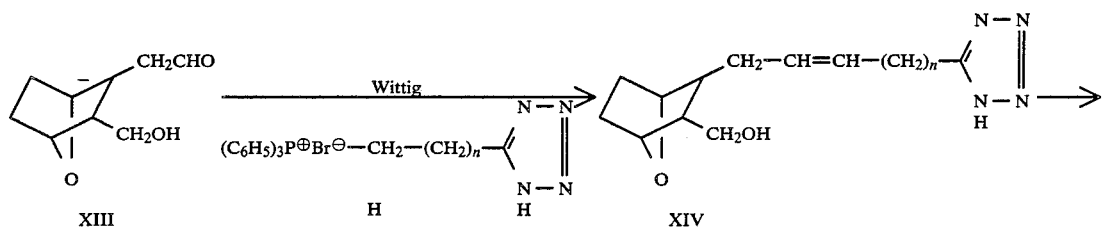

XIII →Wittig→ XIV →

IF

G. Where R is $-\!\!\!\!\begin{array}{c}N\!=\!N\\ \diagup\phantom{xx}\|\\ \phantom{xx}\diagdown\\ N\!-\!N\\ \phantom{xx}H\end{array}$ and A is $(CH_2)_2$

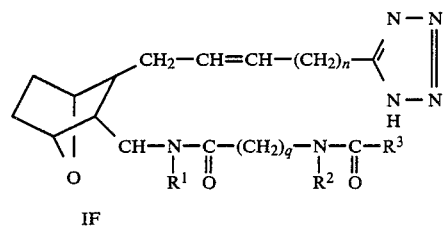

IF →Reduction $H_2$/Pd/C→ IG

H. Where R is $-\!\!\!\!\begin{array}{c}N\!=\!N\\ \diagup\phantom{xx}\|\\ \phantom{xx}\diagdown\\ N\!-\!N\\ \phantom{xx}H\end{array}$ , A is CH=CH, $R^1$ is OH and $R^2$ is H -continued
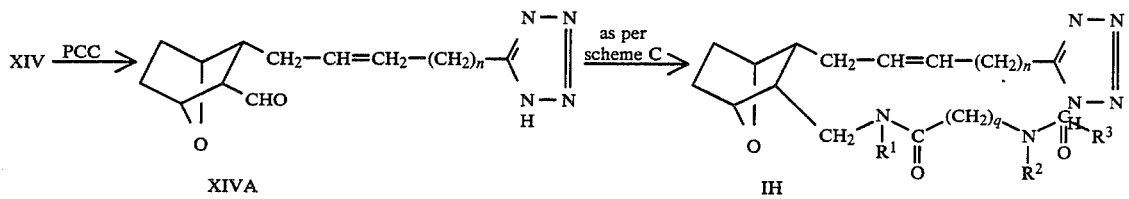
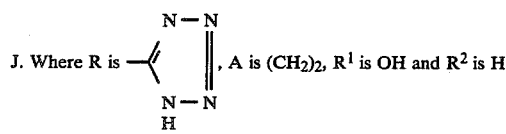
J. Where R is [tetrazole], A is $(CH_2)_2$, $R^1$ is OH and $R^2$ is H
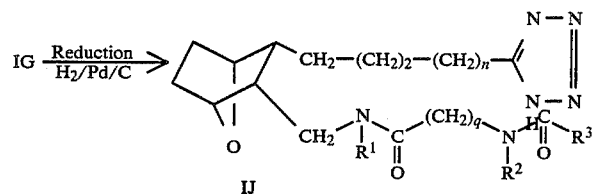
K. Where R is $CH_2OH$
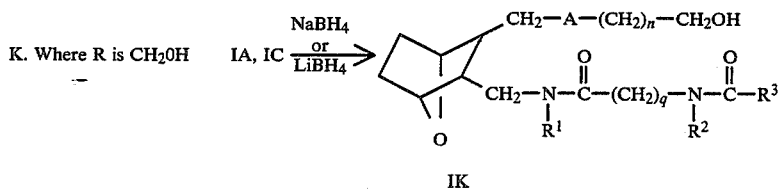
L. Where R is $\overset{O}{\underset{R^4}{C}}N-OR^{5'}$
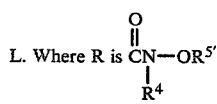
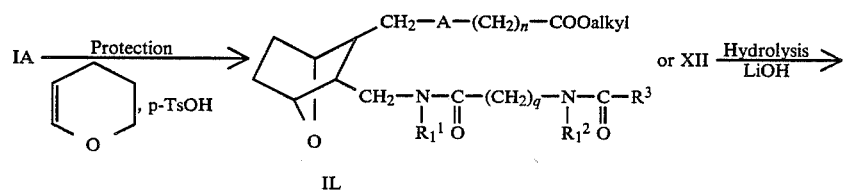
wherein $R_1^1$ or $R_1^2$ is $-O-$[tetrahydropyranyl]
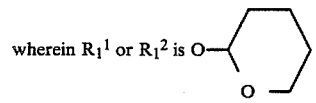
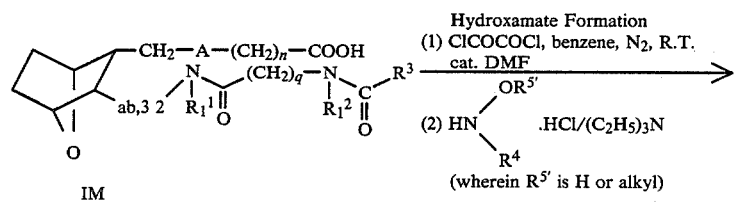
Hydroxamate Formation
(1) ClCOCOCl, benzene, $N_2$, R.T.
cat. DMF
(2) $HN\overset{OR^{5'}}{\underset{R^4}{}}$ · HCl/$(C_2H_5)_3N$
(wherein $R^{5'}$ is H or alkyl)
wherein $R_1^1$ or $R_1^2$ is $-O-$[tetrahydropyranyl]
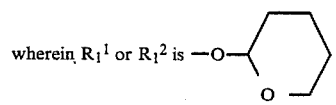

-continued

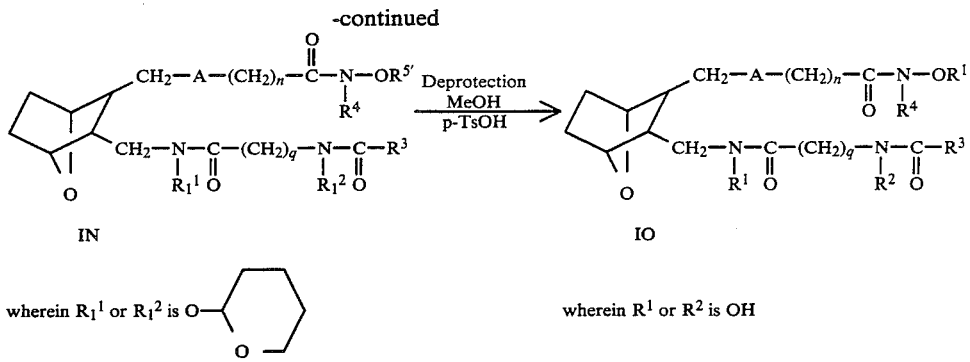

wherein $R_1^1$ or $R_1^2$ is O—[tetrahydropyranyl]

wherein $R^1$ or $R^2$ is OH

As seen in reaction sequence "A", compounds of the invention where R is $CO_2$ alkyl, $R^1$ is H, and $R^2$ is OH, that is

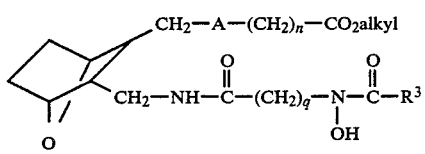

IA are prepared by tosylating the lower alkyl ester containing the hydroxymethyl group, that is, compound II or IIA, (prepared as described in U.S. Pat. No. 4,143,054) by reacting II or IIA with tosyl chloride in the presence of pyridine to form the corresponding tosylate IV which is subjected to a displacement reaction by dissolving IV in dimethylsulfoxide and heating to 90° to 100° C. in the presence of potassium phthalimide to form the phthalimide V. The phthalimide V is then made to undergo selective hydrolysis by dissolving V in methylene chloride and ethanol under an inert atmosphere such as argon and reacting with anhydrous hydrazine to form the amine VI

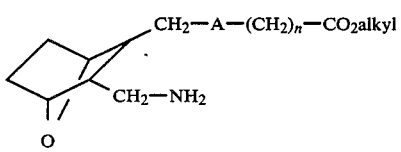

VI

The amine VI is then subjected to a DCC (dicyclohexyl carbodiimide) coupling reaction by reacting VI with acid VII

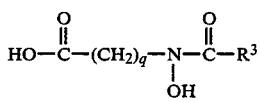

VII in the presence of an inert organic solvent such as tetrahydrofuran and dicyclohexyl carbodiimide under an inert atmosphere, such as argon, employing a molar ratio of VI:VII of within the range of from about 1:1 to about 1:1.2, to form the amide ester compound of the invention IA.

Referring to reaction sequence "B", there is shown a series of reactions for preparing starting material VII. As seen in reaction sequence "B", t-butylbromoalkanoate A is reacted with amine B in the presence of sodium carbonate to form the reaction product C which is dissolved in ethyl ether, sodium bicarbonate and water and treated with acid chloride D to form E. Compound E is then cooled and treated with trifluoroacetic acid to form VII.

The starting acid XI

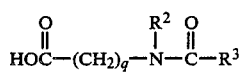

XI may be prepared by reacting the amino acid B'

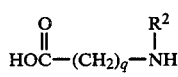

B' or its acid chloride with acid chloride B"

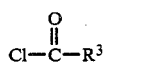

B"

(or its acid if the acid chloride of B' is employed) in the presence of a strong base such as NaOH and water.

As seen in reaction sequence "C", compounds of the invention where R is $CO_2$ alkyl, $R^1$ is OH and $R^2$ is H, that is

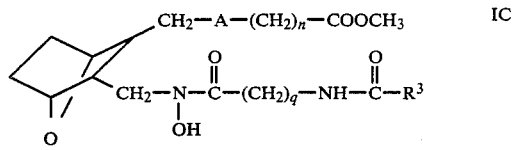

IC are prepared by treating aldehyde VIII

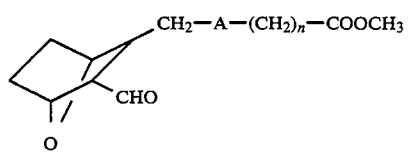

VIII with amine F

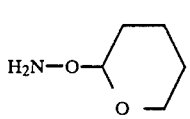

F in the presence of solvent such as methanol to form ester IX

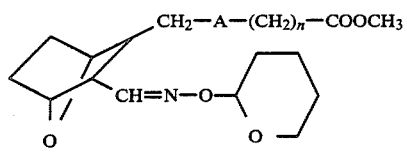   IX which is reduced by treating IX with reducing agent such as sodium cyanoborohydride in the presence of acetic acid and methanol to form ester X

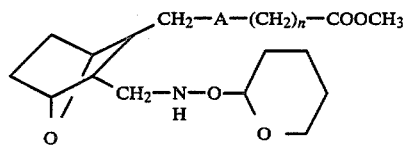   X

Ester X is then subjected to a CDI (carbonyldiimidazole) coupling reaction by reacting X with acid XI

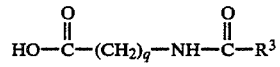   XI in the presence of an inert organic solvent such as tetrahydrofuran and carbonyldiimidazole under an inert atmosphere, such as argon, employing a molar ratio of X:XI of within the range of from about 1:1 to about 1:1.2 to form the amide ester XII which is treated with p-toluene sulfonic acid in the presence of methanol (under argon) to form ester compound of the invention IC.

In reaction sequence "D", amides of the invention of structure IE

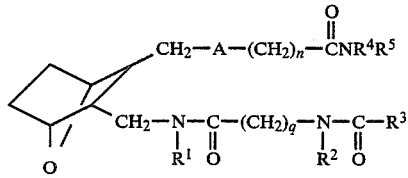   IE wherein $R^4$ and $R^5$ are independently H, alkyl or aryl are prepared by treating ester IA or IC with an amine of the structure $HNR^4R^5$   G Compounds of the invention wherein R is tetrazole

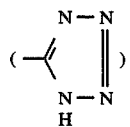

and A is CH=CH are prepared as described in reaction sequence "E" wherein alcohol XIII

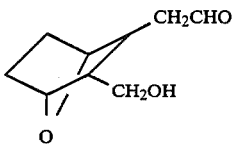   XIII (prepared as described in U.S. Pat. No. 4,143,054) is reacted with a Wittig reagent of the structue H

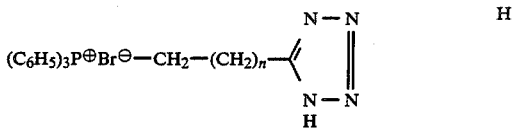   H in the presence of a base, such as potassium t-butoxide or sodium hydride-dimethyl sulfoxide employing a molar ratio of XIII:H of within the range of from about 1:1 to about 0.2:1 to form the hydroxymethyl compound XIV

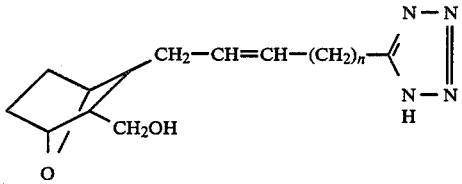   XIV which may then be employed in reaction sequences "A" and "C" in place of compounds II or IIA to form compounds of the invention IF where A is —CH=CH— or IG where A is $(CH_2)_2$

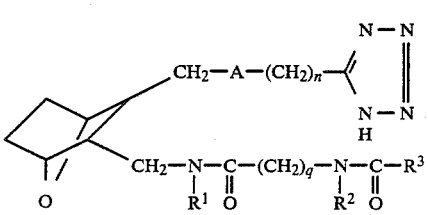   IF or IG

Alternatively, compound IG may be prepared by reducing compound IF by treating with $H_2$ in the presence of palladium on charcoal.

Compounds of the invention wherein R is tetrazole and A is HC=CH, $R^1$ is OH and $R^2$ is H were prepared as described in scheme H wherein alcohol XIV is oxidized

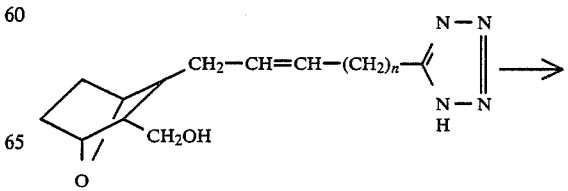

XIV

-continued

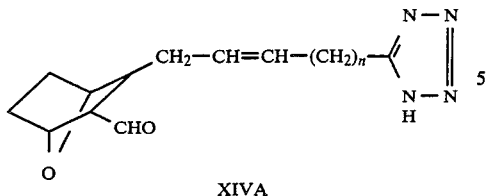

XIVA to the aldehyde XIVA using, for example, PCC (pyridinium chlorochromate) in an inert solvent, such as methylene chloride. Aldehyde XIVA is then carried on to IH using the sequence outlined in scheme C.

Compound of the invention wherein R is tetrazole and A is $(CH_2)_2$, $R^1$ is OH and $R^2$ is H, are prepared as described in scheme J wherein acid IG is reduced with hydrogen in the presence of a catalyst, i.e., palladium on carbon to afford IJ.

As seen in reaction sequence "K", compounds of the invention wherein R is $CH_2OH$ may be prepared by reducing esters IA or IC by treatment with sodium borohydride or lithium borohydride to form compounds of the invention IK

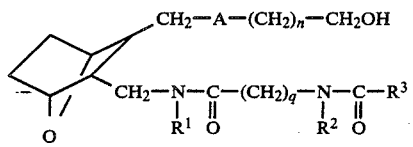

In the reaction sequence identified as "L" Formula I compounds wherein R is

wherein $R^{5'}$ is H or alkyl may be prepared as follows.

Ester I or XII is hydrolyzed with aqueous base, for example, LiOH or NaOH in THF/alcohol mixtures to afford acid IM. Ester IL is prepared by protection of IA as a tetrahydropyranyl ether using dihydropyran and an acid catalyst such as p-TsOH.

A solution of acid IM dissolved in an inert organic solvent such as benzene is treated with oxalyl chloride and a catalytic amount of dimethylformamide (DMF) and the mixture is stirred at room temperature under nitrogen. The resulting acid chloride is dissolved in an inert organic solvent such as tetrahydrofuran and the so-formed solution is added dropwise into a cold solution of amine hydrochloride J

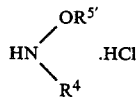

(wherein $R^{5'}$ is H or alkyl, employing a molar ratio of acid chloride:J of within the range of from about 0.3:1 to about 1:1 and preferably from about 0.5:1) and triethylamine in aqueous tetrahydrofuran to form the hydroxamate IN.

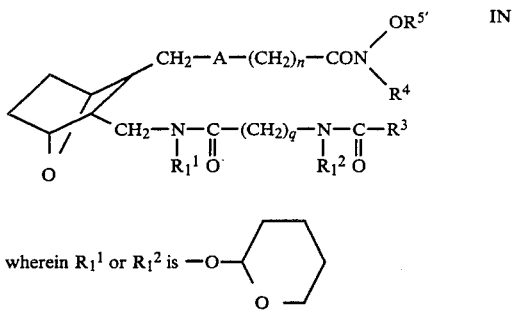

Hydroxamate IN is deprotected by treatment with a lower alcohol, such as, MeOH and an acid catalyst, such as, p-TsOH, to form compound IO

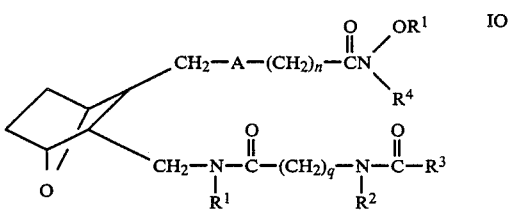

wherein $R^1$ or $R^2$ is OH.

The tris(hydroxymethyl)aminomethane salt of any of the acids of formula I of the present invention is formed by reacting a solution of such acid in an inert solvent such as methanol with tri(hydroxymethyl)aminomethane and thereafter the solvent is removed by evaporation to leave the desired salt.

To form the sulfinyl and/or sulfonyl analogs of compounds of formula I wherein $R^3$ is -S-alkyl, -S-aryl, -S-alkylaryl, -alkyl-S-aryl, alkyl-S-alkyl, or -alkyl-S-alkylaryl, such formula I compounds are subjected to oxidation, for example, by reacting same with sodium periodate or potassium monopersulfate (oxone) in the presence of methanol to form the sulfinyl derivative and/or sulfonyl derivative. Mixtures thereof may be separated by chromatography or other conventional separation procedures.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials following the procedures as outlined in U.S. Pat. No. 4,143,054. Examples of such stereoisomers are set out below.

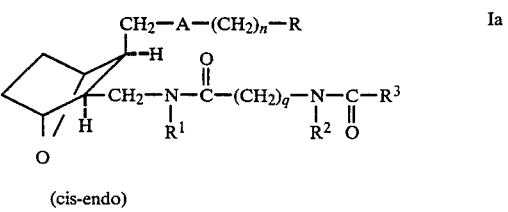

(cis-endo)

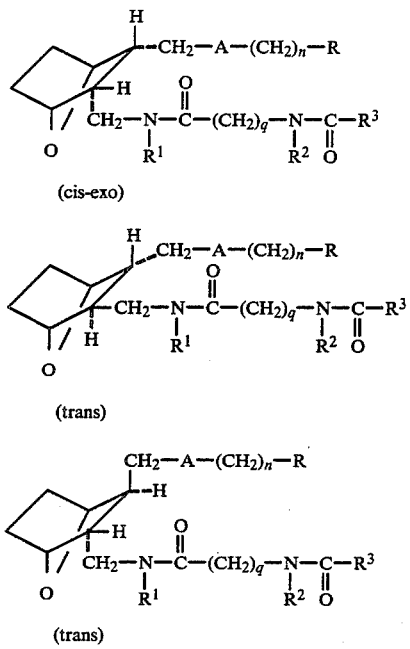

(cis-exo)

(trans)

(trans)

The nucleus in each of the compounds of the invention is depicted as

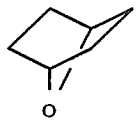

for matter of convenience; it will also be appreciated that the nucleus in the compounds of the invention may be depicted as

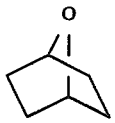

The compounds of this invention are cardiovascular agents useful as platelet aggregation inhibitors, such as in inhibiting arachidonic acid-induced platelet aggregation, e.g., for treatment of thrombotic disease such as coronary or cerebral thromboses, and in inhibiting broncho-constriction. They are also selective thromboxane $A_2$ receptor antagonists and synthetase inhibitors, e.g., having a vasodilatory effect for treatment of myocardial ischemic disease, such as angina pectoris.

The compounds of this invention may also be used in combination with a cyclic AMP phosphodiesterase (PDE) inhibitor such as theophylline or papaverine in the preparation and storage of platelet concentrates.

The compounds of the invention can be administered orally or parenterally to various mammalian species known to be subject to such maladies, e.g., humans, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionaly serve as intermediates for other members of the group.

The compounds of the invention may also be administered topically to treat peripheral vascular diseases and as such may be formulated as a cream or ointment.

The following Examples represent preferred embodiments of the present invention. Unless otherwise indicated, all temperatures are expressed in degrees Centigrade.

EXAMPLE 1

[1S-[1α,2β(5Z),3β,4α]]-7-[3-[[[[Hydroxy(1-oxohexyl)amino]acetyl]methyl]-7-oxabicyclo[2.2.1]hept-2-yl]-5-heptenoic acid, methyl ester A. N-Heptanoyl-N-hydroxy glycine (1) N-(2-Tetrahydropyranyloxy)glycine t-butyl ether Hydroxylamine O-tetrahydropyran ether (1.17 g, 10 mmol) dissolved in distilled tetrahydrofuran (6 ml) was reacted with t-butylbromoacetate (1.95 g, 10 mmol) in the presence of $Na_2CO_3$ (2.21 g, 20 mmol). After stirring at room temperature 5 days, the solids were removed by filtration and washed with EtOAc. The filtrate was taken to dryness in vacuo. The residue was chromatographed on silica gel (50 g, Baker for flash chromatography) eluting with EtOAc-hexane 1:2 to give title ester compound (1.716 g, 74%) as a colorless oil. TLC-silica gel, EtOAc-hexane 1:1 vanillin, Rf=0.58.

(2) t-Butyl-N-heptanoyl-N-(2-tetrahydropyranyloxy)glycinate

Part A (1) ester (1.44 g, 6.23 mmol) was dissolved in $Et_2O$ (30 ml), $NaHCO_3$ (2.12 g, 25 mmol) and $H_2O$ (30 ml) were added. The mixture was cooled in an ice bath and a solution of heptanoyl chloride (1.05 ml, 6.85 mmol) in $Et_2O$ (5 ml) was added dropwise. The cooling bath was removed and the mixture was stirred at room temperature 2 hours. The layers were separated. The ether layer was washed with NaCl solution (25 ml), dried ($MgSO_4$), leaving title ester as an oil (2.15 g, quant.). TLC: silica gel, $Et_2O$-hexane 1:1, PMA, Rf=0.55.

(3) N-Heptanoyl-N-hydroxy glycine

Part A (2) ester (1.10 g, 3.2 mmol) was cooled in an ice bath and treated with precooled distilled trifluoroacetic acid (15 ml). The solution was stirred at 0°-5° C. for 5 hours. The trifluoroacetic acid was removed in vacuo. The residue was partially dissolved in $Et_2O$ (30 ml). The product was extracted into 2N NaOH solution (2×20 ml). The basic extracts were washed with $Et_2O$ (20 ml) and then acidified with concentrated HCl. The desired acid was extracted with EtOAc (3×30 ml), washed with saturated NaCl solution (15 ml), dried ($MgSO_4$), filtered and freed of solvent in vacuo leaving a tan solid (647 mg). This was recrystallized from EtOAc (10 ml) to give title compound as a white solid (486 mg, 75%), m.p. 136°-138° dec.

B. [1S-[1α,2β(5Z),3β,4α]]-7-[3-(Tosyloxymethyl)-7-oxabicyclo[2.2.1]hept-2-yl]-5-heptenoic acid, methyl ester Tosyl chloride (4.256 g, 22.4 mmol) dissolved in CH$_2$Cl$_2$ (30 ml) was added dropwise to a magnetically stirred solution of [1S-[1α,2β(5Z),3β,4α]]-7-[3-(hydroxymethyl)-7-oxabicyclo[2.2.1]hept-2-yl]-5-heptenoic acid, methyl ester (prepared as described in U.S. Pat. No. 4,143,054 (3 g, 11.2 mmol) in pyridine (30 ml) at 0° C. After completion of the addition, the reaction was warmed to room temperature and stirred overnight. The reaction was poured into ice/H$_2$O and stirred for 30 minutes. The products were extracted with EtOAc (80 ml×3). The combined EtOAc layers were washed with 3N-HCl (40 ml×3), saturated NaHCO$_3$, brine and dried over MgSO$_4$. Filtration and evaporation of solvent gave a white solid, which was crystallized from isopropyl ether to give the corresponding title tosylate in the form of needle crystals (4.23 g, 89%), m.p. 68°–70° C.

C. [1S-[1α,2β(5Z),3β,4α]]-7-[3-(Aminomethyl)-7-oxabicyclo[2.2.1]hept-2-yl]-5-heptenoic acid, methyl ester The title B tosylate was subjected to a Gabriel synthesis to form the corresponding amino compound as described below.

The potassium phthalimide used was purified prior to use by boiling 5 g thereof with 9 ml acetone for 15 minutes, filtering while hot and washing with 5 ml acetone. The remaining solid was dried in vacuo for 6 hours at 100° C. prior to use.

The title B tosylate (8.11 g, 19.2 mmol) and purified potassium phthalimide (6.4 g, 34.6 mmol, 1.8 equiv.) in dimethylsulfoxide (70 ml, Burdick & Jackson) were heated at 90°–100° C. for 2¼ hours (checked by TLC Et$_2$O-pet ether 2:1, no tosylate remaining). After cooling to room temperature, water (90 ml) was added. Material began precipitating. The mixture was poured into ice water (~350 ml) and stirred 30 minutes. The straw colored solid was harvested by filtration and washed with more water. The solid was dissolved in warm ethyl acetate (150 ml), washed with water (3×50 ml), dried (MgSO$_4$), filtered and freed of solvent in vacuo. The remaining solid (7.88 g) was recrystallized from isopropyl ether (~150 ml) to give corresponding phthalimide (6.35 g, 83%) TLC. Et$_2$O-hexane 2:1, UV+vanillin R$_f$=0.38, trace 0.09.

The above phthalimide (5.05 g, 13.8 mmol) was dissolved in distilled CH$_2$Cl$_2$ (24 ml) and distilled ethanol (104 ml) in an argon atmosphere. Anhydrous hydrazine (0.78 ml, 25.6 mmol) was added. The mixture was stirred at room temperature. After 8 hours an additional 0.2 ml of hydrazine was added and the mixture was stirred an additional 15 hours at room temperature. A white solid was removed by filtration and washed with more CH$_2$Cl$_2$. The filtrate was taken to dryness in vacuo (on the pump at end). Cold 0.5N HCl solution (80 ml) was added. A small amount of white solid was removed by filtration and washed with additional 0.5N HCl solution (80 ml). The acidic solution was washed with ether (2×100 ml) and then basified with solid K$_2$CO$_3$. The amine was extracted into CHCl$_3$ (3×100 ml), dried (MgSO$_4$) and freed of solvent in vacuo leaving a yellow oil. Ether (100 ml) was added to this oil. Some solid was insoluble. After cooling in an ice bath, the solid was removed by filtration. The solvent was removed from the filtrate in vacuo leaving title amine as a pale yellow oil (2.441 g, 71%). NMR spectra and TLC indicated some minor impurities. The material was used without further purification.

D. [1S-[1α,2β(5Z),3β,4α]]-7-[3-[[[[Hydroxy(1-Oxohexyl)amino]acetyl-amino]methyl]-7-oxabicyclo[2.2.1]hept-2-yl]-5-heptenoic acid, methyl ester Part C chiral amine (411 mg, 1.54 mmol) and Part A acid (325 mg, 1.6 mmol) were largely dissolved in distilled tetrahydrofuran (20 ml) in an argon atmosphere. The mixture was cooled in an ice bath and dicyclohexylcarbodiimide (330 mg, 1.6 mmol) was added. After stirring cold for 2 hours, the reaction mixture was left stirring overnight at room temperature. The solvent was removed in vacuo. Ethyl acetate (8 ml) was added to the residue. After cooling in an ice bath, the solid was removed by filtration and washed with additional cold EtOAc (8 ml). The filtrate was taken to dryness leaving a yellow oil (730 mg). This was chromatographed on silica gel (20 g Baker for flash chromatography) eluting with ether and then 2% methanol in ether to give title methyl ester (455 mg, 65%) as an oil. TLC: silica gel, 5% MeOH in CH$_2$Cl$_2$, vanillin, Rf=0.32.

EXAMPLE 2

[1S-[1α,2β(5Z),3β,4α]]-7-[3-[[[[Hydroxy(1-oxohexyl)a acetyl]amino]methyl]-7-oxabicyclo[2.2.1]hept-2-yl]-5-heptenoic acid The Example 1 methyl ester (452 mg, 1 mmol) was dissolved in distilled THF (40 ml) and water (8 ml) in an argon atmosphere 1N LiOH solution (9.5 ml) was added and the mixture was stirred at room temperature for 3¾ hours. After neutralization with 1N HCl (9.5 ml), solid KCl was added and the layers were separated. The aqueous layer was reextracted with CHCl$_3$ (3×50 ml). The combined organic layers (THF+CHCl$_3$) were washed with saturated NaCl solution (2×25 ml), dried (MgSO$_4$), and freed of solvent in vacuo leaving a viscous oil. This was chromatographed on silica gel (Silicar CC4) (20 g) packed in CH$_2$Cl$_2$. The product was eluted with 2–5% MeOH in CH$_2$Cl$_2$ to give title compound as a viscous oil (326 mg, 74%). This was recrystallized from acetonitrile (~10 ml) to give title acid, 248 mg, 61%, m.p. 119°–121° C.). TLC: silica gel, 10% MeOH in CH$_2$Cl$_2$, vanillin, R$_f$=0.43. [α]$_D$=−5.7° (C=1.4, MeOH).

Anal Calcd for C$_{23}$H$_{38}$O$_6$N$_2$·2H$_2$O: C, 62,47; H, 8.75; N, 6.34. Found: C, 62.28; H, 8.74; N, 6.37.

EXAMPLE 3

[1S-[1α,2β(5Z),3β,4α]]-7-[3-[[Hydroxy-[[(1-oxoheptyl)amino]acetyl]amino]methyl]-7-oxabicyclo[2.2.1]hept-2-yl]-5-heotenoic acid, methyl ester A. N-Hexanoylglycine Glycine (7.5 g, 100 mmol) was dissolved in NaOH solution (NaOH:8 g, H$_2$O:50 ml) and cooled to 0° C. Et$_2$O (50 ml) was added and n-hexanoyl chloride (13.4 g, 100 mmol) was then added dropwise over 60 minutes at 0° C. under vigorous stirring. The reaction was allowed to warm to room temperature and was stirred for 1 hour. 1N-NaOH (10 ml) was added and the layers were separated. The water layer was washed with Et$_2$O (20 ml×2). The combined Et$_2$O layers were extracted with 1N-NaOH (20 ml). The combined water layers were acidified with concentrated HCl to pH 2 and the products were extracted with Et$_2$O (100 ml×3). The combined Et$_2$O layers were washed with brine (50 ml) and dried over MgSO$_4$. Filtration and evaporation of solvent gave a colorless solid (16.2 g), which was crystallized from EtOAc (60 ml) to give colorless needle crystals (10.9 g, 63 mmol, 63%), m.p. 93°–96°. TLC:

silica gel, MeOH, CH$_2$Cl$_2$, HCOOH; 10, 89.5, 0.5, PMA R$_f$=0.45.

B. [1S-[1α,2β(5Z),3β,4α]]-7-[3-[[N-[2-tetrahydropyranyloxy]imino]methyl]-7-oxabicyclo[2.2.1]hept-2-yl]-5-heptenoic acid, methyl ester

[1S-[1α,2β(5Z),3β,4α]]-7-[[3-Formyl]-7-oxabicyclo[2.2.1]hept-2-yl]-5-heptenoic acid, methyl ester (532 mg, 20 mmol) was reacted with hydroxyamine O-tetrahydropyran ether (390 mg, 2.2 mmol) in methanol (20 ml) overnight at room temperature. After removal of the solvent in vacuo, the product was chromatographed on silica gel (45 g, Baker for flash chromatography) eluting with ethyl acetate-hexane (1:3) to give pools containing the isomers of the title compound (528 mg, 72%). The structure was confirmed by NMR.

C. [1S-[1α,2β(5Z),3β,4α]]-7-[3-[[N-[2-tetrahydropyranyloxy]amino]methyl]-7-oxabicyclo[2.2.1]hept-2-yl]-5-heptenoic acid, methyl ester Part B ester compound (548 mg, 1.5 mmol) was dissolved in methanol (10 ml) and NaCNBH$_3$ (234 mg, 3.72 mmol) was added. The solution was cooled in an ice bath and a mixture of acetic acid (7.7 ml) and methanol (7 ml) was added dropwise over a period of 1 hour. The mixture was left overnight at room temperature. Saturated NH$_4$Cl solution (3.5 ml) was added and the mixture was stirred 1 hour at room temperature. Most of the methanol was removed in vacuo. Ethyl acetate (50 ml) was added to the residue and this was washed with 1N NaOH (3×20 ml), saturated NH$_4$Cl solution (2×20 ml) and saturated NaCl solution (20 ml). After drying (MgSO$_4$), the solvent was removed in vacuo leaving an oil (533 mg). This was chromatographed on silica gel (30 g, Baker for flash chromatography), eluting with EtOAc-hexane 1:2 to give title compound (426.7 mg, 77%) as a colorless oil. TLC: silica gel, EtOAc-hexane 1:1, vanillin Rf=0.29.

D. [1S-[1α,2β(5Z),3β,4α]]-7-[3-[[N-2-Tetrahydropyranyloxy[(1-oxoheptyl)amino]acetyl]amino]methyl]-7-oxabicyclo[2.2.1]hept-2-yl]-5-heptenoic acid, methyl ester Part A acid (468 mg, 2.5 mmol) was dissolved in distilled tetrahydrofuran (15 ml) and cooled in an ice bath in an argon atmosphere. Carbonyldiimidazole (405 mg, 2.5 mmol) was added and the mixture was stirred cold for 1 hour and stirred at room temperature for 1 hour. The mixture was again cooled in an ice bath and a solution of Part C ester (460 mg, 1.25 mmol) in distilled tetrahydrofuran (10 ml) was added. The mixture was stirred at room temperature and followed by TLC. After 44 hours the solvent was removed in vacuo. The residue was dissolved in CHCl$_3$ (50 ml) and washed with 1N HCl solution (25 ml), 1N NaOH solution (25 ml) and saturated NaCl solution (25 ml). After drying (MgSO$_4$), the solvent was removed in vacuo leaving an oil (695 mg). This was chromatographed on silica gel (50 g, Baker for flash chromatography) eluting with EtOAc-hexane (1:2 to 2:1) to give title ester (552.2 mg, 82%) as a colorless oil. TLC: silica gel, EtOAc-hexane 1:1, vanillin, Rf=0.18.

E. [1S-[1α,2β(5Z),3β,4α]]-7-[3-[[Hydroxy[[1-oxoheptyl)amino]acetyl]amino]methyl]-7-oxabicyclo[2.2.1]hept-2-yl]-5-heptenoic acid, methyl ester Part D compound (550 mg, 1.02 mmol) was dissolved in methanol (30 ml) in an argon atmosphere. p-Toluene sulfonic acid.H$_2$O (10 mg) was added and the mixture was stirred at room temperature 22 hours. TLC indicated a small amount of Part D compound remained and additional p-toluene sulfonic acid (30 mg) was added and the mixture was stirred another 8 hours. Saturated NaHCO$_3$ solution (20 ml) was then added and most of the methanol was removed in vacuo. EtOAc (50 ml) was added and the layers were separated. The organic layer was washed with saturated NaHCO$_3$ solution (15 ml) and saturated NaCl solution (15 ml), dried (MgSO$_4$) and freed of solvent in vacuo leaving an oil (471 mg). This was chromatographed on silica gel (20 g, Baker for flash chromatography) eluting with 1–2% MeOH in CH$_2$Cl$_2$ to give title ester (367 mg, 79%) TLC: silica gel, 5% MeOH in CH$_2$Cl$_2$, vanillin Rf=0.49.

EXAMPLE 4

[1S-[1α,2β(5Z),3β,4α]]-7-[3-[[Hydroxy[[(1-oxoheptyl)amino]acetyl]amino]methyl]-7-oxabicyclo[2.2.1]hepty-2-yl]-5-heptenoic acid Example 3 methyl ester (367 mg, 0.81 mmol) was dissolved in distilled THF (20 ml) and water (4.8 ml) in an argon atmosphere. 1N LiOH solution (4.9 ml) was added and the mixture was stirred at room temperature 5 hours. The mixture was neutralized with 1N HCl solution (4.9 ml) and solid KCl was added. The layers were separated. The crude crystalline product (338 mg, 95%) was recrystallized from CH$_3$CN (10 ml) to give title acid as white crystalline material (247.3 mg, 70%), m.p. 104°–108° C. [α]$_D$=−4.2° (c=0.74, MeOH). TLC: silica gel, 10% MeOH in CH$_2$Cl$_2$, vanillin, Rf=0.52.

Anal Calcd for C$_{23}$H$_{38}$O$_6$N$_2$: C, 62.99; H, 8.73; N, 6.39. Found: C, 63.12; H, 8.63; N, 6.40.

EXAMPLE 5

[1S-(1α,2β,3β,4α)]-7-[3-[[[[Hydroxy(1-Oxohexyl)amino]acetyl]amino]methyl]-7-oxabicyclo[2.2.1]hept-2-yl]heptanoic acid A. [1S-(1α,2β,3β,4α)]-7-[3-(Hydroxymethyl)-7-oxabicyclo[2.2.1]hept-2-yl]heptanoic acid, methyl ester To 800 mg (3.0 mmole) of the [1S-[1α,2β(Z),3β,4α]]-7-[3-(hydroxymethyl)-7-oxabicyclo[2.2.1]hept-2-yl]-5-heptenoic acid, methyl ester dissolved in 120 ml of ethyl acetate was added, under an argon atmosphere, 160 mg of 5% Pd on carbon. The argon atmosphere was exchanged for a slight positive pressure of hydrogen and the reaction was stirred for 8 hours at 25°, filtered through a celite plug and evaporated to provide 730 mg (90%) of the title A compound.

B. [1S-(1α,2β,3β,4α)]-7-[3-[[[[Hydroxy(1-oxohexyl)amino]acetyl]amino]methyl]-7-oxabicyclo[2.2.1]hept-2-yl]heptanoic acid, methyl ester Following the procedure of Examples 1 and 2 except substituting the Part A alcohol-ester for the alcohol ester employing in Example 1 Part B, the title product is obtained.

EXAMPLE 6

[1S-[1β,2α(5Z),3α,4β]]-7-[3-[[[[Hydroxy(1-Oxopropyl)amino]acetyl]amino]methyl]-7-oxabicyclo[2.2.1]hept-2-yl]-5-heptenoic acid Following the procedure of Examples 1 and 2 except substituting propanoyl chloride for hexanoyl chloride, the title compound is obtained.

EXAMPLE 7

[1S-[1β,2α(5Z),3α,4β]]-7-[3-[[[[Hydroxy(1-Oxoethyl)amino]acetyl]amino]methyl]-7-oxabicyclo[2.2.1]hept-2-yl]-5-heptenoic acid Following the procedure of Examples 1 and 2 except substituting acetyl chloride for hexanoyl chloride, the title compound is obtained.

EXAMPLE 8

[1S-[1β,2α(5Z),3α,4β]]-7-[3-[[[[Hydroxy(1-Oxo-2-butenyl)amino]acetyl]amino]methyl]-7-oxabicyclo[2.2.1]hept-2-yl]-5-heptenoic acid Following the procedure of Examples 1 and 2 except substituting 2-butenoyl chloride for hexanoyl chloride, the title compound is obtained.

EXAMPLE 9

[1S-[1β,2α(5Z),3α,4β]]-7-[3-[[[[Hydroxy(1-Oxo-3-butynyl)amino]acetyl]amino]methyl]-7-oxabicyclo[2.2.1]hept-2-yl]-5-heptenoic acid Following the procedure of Examples 1 and 2 except substituting 3-butynoyl chloride for hexanoyl chloride, the title compound is obtained.

EXAMPLE 10

[1S-1β,2α(5Z),3α,4β]]-7-[3-[[Hydroxy-[[(1-oxopropyl)amino]acetyl]amino]methyl]-7-oxabicyclo[2.2.1]hept-2-yl]-5-heptenoic acid Following the procedure of Examples 3 and 4 except substituting propanoyl chloride for hexanoyl chloride, the title compound is obtained.

EXAMPLE 11

[1S-[1β,2α(5Z),3α,4β]]-7-[3-[[(Hydroxy-[[(1-Oxo-2-butenyl)amino]acetyl]amino]methyl]-7-oxabicyclo[2.2.1]hept-2-yl]-5-heptenoic acid Following the procedure of Examples 3 and 4 except substituting 2-butenoyl chloride for hexanoyl chloride, the title compound is obtained.

EXAMPLE 12

[1S-1β,2α(5Z),3α,4β]]-7-[3-[[[[Hydroxy(1-oxooctyl)amino]acetyl]amino]methyl]-7-oxabicyclo[2.2.1]hept-2-yl]-5-heptenoic acid Following the procedure of Examples 1 and 2 except substituting octanoyl chloride for hexanoyl chloride, the title compound is obtained.

EXAMPLE 13

1S-(1β,2α,3α,4β)]-7-[3-[[[[Hydroxy(1-Oxobutyl)amino]acetyl]amino]methyl]-7-oxabicyclo[2.2.1]hept-2-yl]heptanoic acid Following the procedure of Example 5 except substituting butanoyl chloride for hexanoyl chloride, the title compound is obtained.

EXAMPLE 14

[1S-(1β,2α,3α,4β)]-7-[3-[[[[Hydroxy(1-Oxo-2-propenyl)amino]acetyl]amino]methyl]-7-oxabicyclo[2.2.1]hept-2-yl]heptanoic acid Following the procedure of Example 5 except substituting propenoyl chloride for hexanoyl chloride, the title compound is obtained.

EXAMPLE 15

[1S-(1β,2α,3α,4β)]-7-[3-[[Hydroxy(1-Oxoheptyl)amino]acetyl]amino]methyl]-7-oxabicyclo[2.2.1]hept-2-yl-]heptanoic acid Following the procedure of Example 5 except substituting heptanoyl chloride for hexanoyl chloride, the title compound is obtained.

EXAMPLE 16

[1S-[1β,2α(Z),3α,4β]]-6-[3-[[[[Hydroxy(1-Oxohexyl)amino]acetyl]amino]methyl]-7-oxabicyclo[2.2.1hept-2-yl]-1-(1H-tetrazol-5-yl)-4-hexene A. [1S-[1β,2α(Z),3α,4β]]-6-[3-Hydroxymethyl-7-oxabicyclo[2.2.1]hept-2-yl]-1-(1H-tetrazol-5-yl)-4-hexene To 5.5 g (11.8 mmole) of triphenyl-4-(1H-tetrazol-5-yl)butyl phosphonium bromide in 100 ml of tetrahydrofuran (THF) at 0° is added 2.78 g (23.6 mmole) potassium t-butoxide. The reaction is stirred at 25° for 30 minutes and (exo)octahydro-5,8-epoxy-1H-benzopyran-3-ol, (2 g, 11.8 mmole, prepared as described in U.S. Pat. No. 4,143,054) is added in 30 ml of THF. The reaction is stirred for 2 hours and quenched with dilute aqueous HCl. The aqueous layer is extracted with 250 ml of ethyl acetate. The combined organic solutions are evaporated in vacuo, diluted with 500 ml of a 5% NaHCO₃ solution, washed with 100 ml of ether, acidified with dilute HCl to pH 3, and extracted with three 500 ml portions of ethyl acetate. The combined organic solutions are dried over anhydrous MgSO₄, and purified by silica chromatography using a 5% methanol in methylene chloride eluant to provide title A compound.

B. [1S-[1β,2α(5Z),3α,4β]]-6-[3-[[[[(1-Oxohexyl)amino]acetyl]amino]methyl]-7-oxabicyclo[2.2.1]hept-2-yl]-1-(1H-tetrazol-5-yl)-4-hexene Following the procedure of Examples 1 and 2 except substituting the Part A compound for the hydroxymethyl compound used in Example 1 Part B, the title compound is obtained.

EXAMPLE 17

[1S-[1β,2α(5Z),3α,4β]]-7-[3-[[Hydroxy-]](1-Oxohexyl)amino]acetyl]amino]methyl]-7-oxabicyclo[2.2.1]hept-2-yl]-N-hydroxy-N-methyl-5-heptenamide A solution of Example 4 acid (0.82 mmole) in dry benzene (5.0 ml) is treated with oxalyl chloride (1 ml; 11.24 mmole or 13.7 eq.) and a drop of DMF, and stirred at room temperature under nitrogen for 2 hours The excess oxalyl chloride and solvent are blown off by a stream of nitrogen while heating the reaction flask in a warm water bath and the oil obtained dried in vacuo (oil pump) for 1 hour. The residual acid chloride is dissolved in dry tetrahydrofuran (1.5 ml) and added dropwise into a cold solution (0°, ice-water) of 98% methylhydroxylamine hydrochloride (139.8 mg; 1.64 mmole; 2 eq.) and triethylamine (0.34 ml; 2.46 mmole; 3 eq.) in tetrahydrofuran (2 ml) and water (2.0 ml). The mixture is stirred at 0° under nitrogen for 30 minutes and at room temperature for 5.5 hours, diluted with water (10 ml) and extracted twice with dichloromethane (50 ml). The organic extract is washed with 1N HCl (10 ml), 5% NaHCO₃ (5 ml) and water (10 ml), dried (anhydrous MgSO₄), filtered and evaporated to dryness giving the crude product, which is purified by silica gel column to afford the title compound.

EXAMPLE 18

[1S-[1β,2α(5Z),3α,4β]]-7-[3-[[[[Hydroxy(1-Oxo-4phenyl)butyl]amino]acetyl]amino]methyl]-7-oxabicyclo[2.2.1]hept-2-yl]-5-heptenoic acid

A. 4-Phenylbutanoyl glycine ethyl ester

4-Phenylbutyric acid (2.46 g, 15 mmol) was dissolved in distilled THF (70 ml) in an argon atmosphere. After cooling in an ice bath, carbonyldiimidazole (CDI) (2.43 g, 1.5 mmol) was added and the mixture was stirred cold 1 hour and at room temperature 1 hour. The mixture was then cooled and glycine ethyl ester.HCl (2.09 g, 15 mmol) and distilled Et₃N (2.1 ml, 15 mmol) were added. The mixture was left stirring overnight at room temperature. After removal of the solvent in vacuo, Et₂O (200 ml) was added. The solution was washed with 1N HCl (70 ml), 0.5 N NaOH (70 ml) and saturated NaCl solution (70 ml), dried (MgSO₄) and freed of solvent in vacuo leaving title compound (3.13 g, 84%) as white crystalline material. TLC: silica gel, Et₂O, UV; $R_f$: 0.58.

B. 4-Phenylbutanoyl glycine

The Part A ester (3.07 g, 12.3 mmol) was hydrolyzed with NaOH (5 g, 125 mmol) in water (60 ml). After stirring at room temperature 6 hours, neutral material was removed by washing with Et₂O (2×50 ml). The aqueous solution was then acidified with concentrated HCl solution. The product was extracted into CHCl₃ (3×60 ml), dried (MgSO₄) and freed of solvent in vacuo leaving a white solid. This was recrystallized from EtOAc (10 ml) to give title compound (2.18 g, 80%), m.p. 99°-101° C.

C. [1S-[1β,2α(5Z),3α,4β]]-7-[3-[[[[Hydroxy-(1-Oxo-4-phenyl)butyl]amino]acetyl]amino]methyl]-7-oxabicyclo[2.2.1hept]-2-yl]-5-heptenoic acid Part B acid (1 mmol) was reacted with DCC (1 mmol) and then with Example 1 Part C chiral amine (1 mmol) as described in Example 1 to produce the title product.

D. [1S-[1β,2α(5Z),3α,4β]]-7-[3-[[[[(1-Oxo-4-phenyl)-butyl]amino]acetyl]amino]methyl]-7-oxabicyclo[2.2.1-]hept-2-yl]-5-heptenoic acid The Part C methyl ester (0.71 mmol) is hydrolyzed with LiOH in a water-THF mixture as described in Example 2 to form title acid.

EXAMPLE 19

[1S-[1α,2β(Z),3β,4α]]-7-[3-[[Hydroxy-[[[(phenylthio)acetyl]amino]acetyl]amino]methyl]-7-oxabicyclo[2.2.1]hept-2-yl]-5-heptenoic acid

A. (Phenylthio)acetyl glycine ethyl ester

The title ethyl ester was prepared from thiophenoxyacetic acid (15 mmol) and the ethyl ester of glycine.HCl using carbonyldiimidazole (CDI) as described in Example 18, Part A giving 2.95 g (78%) of solid.

B. (Phenylthio)acetyl glycine

The Part A ethyl ester was hydrolyzed with aqueous NaOH as described in Example 18 Part B to give the title acid (1.041 g, 92%) as a crystalline material.

C. [1α,2β(Z),3β,4α]]-7-[3-[[Hydroxy[[[(phenylthio)acetyl]amino]acetyl]amino]methyl]-7-oxabicyclo[2.2.1]hept-2-yl]-5-heptenoic acid, methyl ester Following the procedure of Example 3, except substituting the above Part B acid for the Example 3 Part A acid, the title ester is obtained.

D. [1S-[1α,2β(Z),3β,4α]]-7-[3-[[Hydroxy[[[(phenylthio)acetyl]amino]acetyl]amino]methyl]-7-oxabicyclo[2.2.1]hept-2-yl]-5-heptenoic acid The Part C methyl ester (0.98 mmol) is hydrolyzed with 1N LiOH (2 equivalents) as described in Example 4 to form title acid product.

EXAMPLE 20

[1S-[1α,2β(Z),3β,4α]]-7-3-[[[[Hydroxy(phenoxyacetyl)amino]acetyl]amino]methyl]-7-oxabicyclo[2.2.1]hept-2-yl]-5-heptenoic acid

A. Phenoxyacetyl glycine

Glycine (20 mmol) was reacted with distilled phenoxyacetyl chloride (22 mmol) in the presence of NaOH (40 mmol) in a mixture of water and ether as described in Example 5 Part A. The crude product was recrystallized from EtOAc (15 ml) to give title acid (2.38 gm, 57%).

B. [1S-[1α,2β(Z),3β,4α]]-7-[3-[[[[Hydroxy(phenoxyacetyl)amino]acetyl]amino]methyl]-7-oxabicyclo[2.2.1]hept-2-yl]-5-heptenoic acid, methyl ester Part A acid (1.5 mmol) was reacted with DCC (1.5 mmol), followed by Example 1 Part C chiral amine (1.5 mmol) as described in Example 1 to form title product.

C. [1S-[1α,2β(Z),3β,4α]]-7-[3-[[[[Hydroxy(phenoxyacetyl)amino]acetyl]amino]methyl]-7-oxabicyclo[2.2.1]hept-2-yl]-5-heptenoic acid The Part B methyl ester (1.01 mmol) is hydrolyzed with 1N LiOH (2 equivalents) in a THF-H₂O mixture as described in Example 2 to give the title acid.

EXAMPLE 21

[1S-[1α,2β(5Z),3β,4α]]-7-[3-[[Hydroxy-[[(1-oxo-3-phenylpropyl)amino]acetyl]amino]methyl]-7-oxabicyclo[2.2.1]hept-2-yl]-5-heptenoic acid

A. 3-Phenylpropanoyl glycine

Glycine (1.5 g, 20 mmol) and hydrocinnamoyl chloride (3.37 g, 22 mmol) were reacted in the presence of NaOH (40 mmol) in a mixture of water and ether using the method described in Example 5 Part A. The crude product was extracted into chloroform, dried (MgSO₄) and freed of solvent in vacuo leaving a near white solid (3.53 g, 85%). This was recrystallized from EtOAc (13 ml) to give title compound (2.66 g, 64%) m.p. 112°-114° C.

B. [1S-[1α,2β(5Z),3β,4α]]-7-[3[[Hydroxy-[[(1-oxo-3-phenylpropyl)amino]acetyl]amino]methyl]-7-oxabicyclo[2.2.1]hept-2-yl]-5-heptenoic acid, methyl ester Following the procedure of Example 3 except substituting the above Part A acid for the Example 3 Part A acid, the title ester is obtained.

C. [1S-[1α,2β(5Z),3β,4α]]-7-[3-[[Hydroxy[[(1-oxo-3-phenylpropyl)amino]acetyl]amino]methyl]-7-oxabicyclo[2.2.1]hept-2-yl]-5-heptenoic acid The Part B methyl ester (0.72 mmol) is hydrolyzed with LiOH in a water-THF mixture as described in Example 4 to form the title acid.

EXAMPLE 22

[1S-[1α,2β(5Z),3β,4α]]-7-[3-[[[[Hydroxy-(1-oxo-5-phenylpentyl)amino]acetyl]amino]methyl]-7-oxabicyclo[2.2.1]hept-2-yl]-5-heptenoic acid

A. 5-Phenylpentanoyl glycine ethyl ester

5-Phenylvaleric acid (2.67 g, 15 mmol) in distilled THF was reacted with CDI (15 mmol) followed by glycine ethyl ester.HCl (15 mmol) and C₂H₅)₃N (15 mmol) as described in Example 56 Part A. The crude material (3.25 g, 82%) was used without purification.

B. 5-Phenylpentanoyl glycine

The Part A ester (12.34 mmol) was hydrolyzed with NaOH in water as described in Example 56 Part B. The crude product was recrystallized from EtOAc (12 ml) to give title compound (2.39 g, 82%), m.p. 93°–96° C.

C. [1S-[1α,2β(5Z),3β,4α]]-7-[3-[[[[Hydroxy-(1-oxo-5-phenylpentyl)amino]acetyl]amino]methyl]-7-oxabicyclo[2.2.1]hept-2-yl]-5-heptenoic acid, methyl ester Part B compound (1 mmol) is reacted with DCC (1 mmol) and then with Example 1 Part C chiral amine (1 mmol) as described in Example 1 to form title ester.

D. [1S-[1α,2β(5Z),3β,4α]]-7-[3-[[[[Hydroxy-(1-oxa-5-phenylpentyl)amino]acetyl]amino]methyl]-7-oxabicyclo[2.2.1]hept-2-yl]-5-heptenoic acid The Part C methyl ester (0.749 mmol) is hydrolyzed with LiOH in a water-THF mixture as described in Example 2 to form title acid.

EXAMPLE 23

[1S-[1α,2β(Z),3β,4α]]-7-[3-[[[[Hydroxy-[1-oxo-3-(phenylthio)propyl]amino]acetyl]amino]methyl]-7-oxabicyclo[2.2.1]hept-2-yl]-5-heptenoic acid A. 3-(Phenylthio)propanoic acid, methyl ester Thiophenol (440 mg, 4 mmol) and Et$_3$N (70 μl, 0.5 mmol) were dissolved in CH$_2$Cl$_2$ (5 ml). Methyl acrylate (412 mg, 4.8 mmol) was added dropwise. The reaction was exothermic. After stirring at room temperature for 30 minutes, the excess methyl acrylate was removed in vacuo. TLC: silica gel, Et$_2$O-hexane 1:2, UV R$_f$=0.58. The crude title ester was used without further purification.

B. 3-(Phenylthio)propanoic acid

The crude Part A methyl ester (~4 mmole) was treated with 10 ml 1N NaOH and THF (5 ml). After stirring at room temperature 3 hours, ether (30 ml) was added. The layers were separated and the ether layer was reextracted with 1N NaOH solution (10 ml). The combined aqueous layers were washed with Et$_2$O (20 ml) and then acidified with concentrated HCl. The product was extracted with CHCl$_3$ (2×30 ml). The chloroform extracts were washed with saturated NaCl solution (2×20 ml), dried (MgSO$_4$) and freed of solvent in vacuo leaving title acid as a white solid (quant.). This was used without further purification.

C. 3-(Phenylthio)propanoyl glycine ethyl ester

Part B acid (0.740 g, 4.06 mmol) was reacted with carbonyldiimidazole (4.06 mmol) followed by glycine ethyl ester.HCl (4.06 mmol) as described in Example 56 Part A to give the title ester (1.00 g, 92%) as crystalline material.

D. 3-(Phenylthio)propanoyl glycine

The Part C ethyl ester (0.96 g, 3.6 mmol) was hydrolyzed with NaOH solution as described in Example 56 Part B to give a white solid which was triturated with Et$_2$O to give title acid (0.75 g, 87%).

E. [1S-[1α,2β(Z),3β,4α]]-7-[3-[[Hydroxy[[1-oxo-3-(phenylthio)propyl]amino]acetyl]amino]methyl]-7-oxabicyclo[2.2.1]hept-2-yl]-5-heptenoic acid, methyl ester Following the procedure of Example 3 except substituting the above Part D acid for the Example 3 Part A acid, the title ester is obtained.

F. [1S-[1α,2β(Z),3β,4α]]-7-[3-[[Hydroxy[[1-oxo-3-(phenylthio)propyl]amino]acetyl]amino]methyl]-7-oxabicyclo[2.2.1]hept-2-yl]-5-heptenoic acid The Part E methyl ester (1.285 mmol) is dissolved in THF (25 ml) and H$_2$O (2.5 ml) in an argon atmosphere and treated with 1N LiOH solution (2.6 ml). The mixture is stirred at room temperature for 5 hours and then worked up as described in Example 4 to form the title acid.

EXAMPLE 24

[1S-[1α,2β(Z),3β,4α]]-7-[3-[[[[[Hydroxy(phenylmethyl)thio]acetyl]amino]acetyl]amino]methyl]-7-oxabicyclo[2.2.1]hept-2-yl]-5-heptenoic acid A. Chloroacetyl glycine Glycine (1.5 g, 20 mmol) was dissolved in 2N NaOH (25 ml, 50 mmol) and ether (20 ml) was added. Chloroacetyl chloride (2.26 g) dissolved in Et$_2$O (20 ml) was added dropwise at 0° C. The mixture was stirred at 0° for 30 minutes and at room temperature 1 hour. The layers were separated and the water layer was washed with Et$_2$O (2×20 ml). The water layer was then acidified to pH 2 with concentrated HCl and the product was extracted into EtOAc (3×50 ml). The combined EtOAc extracts were washed with brine, dried (MgSO$_4$), and freed of solvent in vacuo to give title acid compound as a solid (2.56 g, 84%) which was used without further purification.

B. (Benzylthio)acetyl glycine

Part A acid (1.28 g, 8.4 mmol) was dissolved in methanol (10 ml) and cooled in an ice bath. Sodium methoxide (1.08 g, 20 mmol) was added followed by dropwise addition of benzyl mercaptan (1.25 g, 10.08 mmoles). After stirring overnight at room temperature, 1N NaOH solution (10 ml) was added. Ether washes (2×40 ml) removed neutral material. The aqueous layer was then acidified to pH 2 with concentrated HCl. The product was extracted with Et$_2$O (3×50 ml), washed with brine, dried (MgSO$_4$) and freed of solvent in vacuo leaving a white solid. This was recrystallized from benzene to give title acid compound (1.28 g, 64%).

C. [1S-[1α,2β(Z),3β,4α]]-7-[3-[[[[[Hydroxy(phenylmethyl)thio]acetyl]amino]acetyl]amino]methyl]-7-oxabicyclo[2.2.1]hept-2-yl]-5-heptenoic acid, methyl ester Part B acid (359 mg, 1.5 mmol) is reacted with DCC (1.5 mmol) followed by Example 1 Part C chiral amine.HCl 3 (1.5 mmol) using the procedure described in Example 1 to form the title compound.

D. [1S-[1α,2β(Z),3β,4α]]-7-[3-[[[[[Hydroxy(phenylmethyl)thio]acetyl]amino]acetyl]amino]methyl]-7-oxabicyclo[2.2.1]hept-2-yl]-5-heptenoic acid The Part C methyl ester (1.28 mmol) is hydrolyzed with 1N LiOH solution (2.6 ml) in a THF-water mixture as described in Example 2 to form the title acid.

EXAMPLE 25

[1S-[1α,2β(Z),3β,4α]]-7-[3-[[Hydroxy-[[[(butylthio)acetyl]amino]acetyl]amino]methyl]-7-oxabicyclo[2.2.1]hept-2-yl]-5-heptenoic acid A. (Butanethio)acetyl glycine Example 24 Part A acid compound (1.28 g, 8.4 mmol) was reacted with 1-butanethiol using the procedure described in Example 64. The crude product was crystallized with diisopropylether (~10 ml) to give title acid (0.55 g, 32%).

B. [1S-[1α,2β(Z),3β,4α]]-7-3-[[Hydroxy[[[(butylthio)acetyl]amino]acetyl]amino]methyl]-7-oxabicyclo[2.2.1]hept-2-yl]-5-heptenoic acid, methyl ester Part A acid (308 mg, 1.5 mmol) is reacted with carbonyldiimidazole (1.5 mmol) followed by Example 1 Part C chiral amine hydrochloride (1.5 mmol) using the procedure described in Example 1 to form the title ester.

C. [1S-[1α,2β(Z),3β,4α]]-7-[3-[[Hydroxy[[[(butylthio)acetyl]amino]acetyl]amino]methyl]-7-oxabicyclo[2.2.1]hept-2-yl]-5-heptenoic acid The Part B methyl ester (1.18 mmol) is hydrolyzed with 1N LiOH solution (2.4 ml) in a tetrahydrofuran-water mixture using the procedure described in Example 1 to form the title acid.

EXAMPLE 26

[1S-[1α,2β(Z),3β,4α]]-7-[3-[[[[[Hydroxy(cyclohexylmethyl)thio]acetyl]amino]acetyl]amino]methyl]-7-oxabicyclo[2.2.1]hept-2-yl]-5-heptenoic acid A. Cyclohexylmethylthiol acetate Cyclohexylmethyl mesylate (1.92 g, 10 mol) and KSCOCH₃ (1.25 g) were suspended in distilled tetrahydrofuran (THF). The reaction mixture was heated under reflux for 3 hours. Additional KSCOCH₃ (1.25 g) and THF (9 ml) were added and the mixture was heated under reflux an additional 3 hours. Et₂O (100 ml) was added and the mixture was washed with brine (30 ml). The aqueous layer was reextracted with Et₂O (30 ml). The combined organic layers were washed with brine (15 ml), dried (MgSO₄) and freed of solvent to give a straw colored oil (1.8 g). This was chromatographed on silica gel (50 g, Baker for flash chromatography) eluting with 2% Et₂O in hexane to give title compound (1.189 g, 69%) as an oil. TLC: silica gel, 10% Et₂O in hexane, UV and I₂, $R_f$=0.48.

B. [(Cyclohexylmethyl)thio]acetyl glycine

Part A compound (6 mmol) and the Example 64 Part A acid (6 mmol) were reacted in the presence of NaOMe (17 mmol) as described in Example 64 Part B. The crude product was crystallized from diisopropyl ether to give title compound (516 mg, 35%).

C. [1S-[1α,2β(Z),3β,4α]]-7-[3-[[[[[Hydroxy(cyclohexylmethyl)thio]acetyl]amino]acetyl]amino]methyl]-7-oxabicyclo[2.2.1]hept-2-yl]-5-heptenoic acid, methyl ester Part B compound (368 mg, 1.5 mmol) was coupled with Example 1 Part C chiral amine.HCl (456 mg, 1.5 mmol) in the presence of DCC (1.5 mmol) as described in Example 1 to form title ester.

D. [1S-[1α,2β(Z),3β,4α]]-7-[3-[[[[[Hydroxy(cyclohexylmethyl)thio]acetyl]amino]acetyl]amino]methyl]-7-oxabicyclo[2.2.1]hept-2-yl]-5-heptenoic acid The Part C methyl ester (1.09 mmol) is hydrolyzed with 1N LiOH (4 ml) in a mixture of THF and water as described in Example 2 to form the title product.

EXAMPLE 27

[1S-[1α,2β(Z),3β,4α]]-7-[3-[[Hydroxy-[[[(phenylsulfinyl)acetyl]amino]acetyl]amino]methyl]-7-oxabicyclo[2.2.1]hept-2-yl]-5-heptenoic acid Powdered NaIO₄ (385 mg, 1.8 mmol) is dissolved in water (12 ml). A solution of Example 19 acid compound (0.6 mmol) in methanol (20 ml) is added. The mixture is stirred overnight at room temperature. Most of the methanol is removed in vacuo. Saturated NaCl solution (50 ml) is added. The product is extracted with CHCl₃ (3×50 ml). The combined chloroform extracts are washed with NaCl solution (20 ml), dried (MgSO₄), and freed of solvent in vacuo leaving an oil. This is chromatographed on silica gel (4 g, Baker for flash chromatography) eluting with 5% MeOH in CH₂Cl₂ to give title compound.

EXAMPLE 28

[1S-[1α,2β(Z),3β,4α]]-7-[3-[[Hydroxy-[[[(phenylsulfonyl)acetyl]amino]acetyl]amino]methyl]-7-oxabicyclo[2.2.1]hept-2-yl]-5-heptenoic acid Example 19 acid compound (0.9 mmol) is dissolved in methanol (10 ml) and cooled in an ice bath. Oxone (810 mg ~2.7 mmol) dissolved in water (10 ml) is added. The mixture is stirred at room temperature 4 hours, then diluted with water (30 ml). The product is extracted into CHCl₃ (3×35 ml). The combined CHCl₃ extracts are washed with saturated NaCl solution (2×20 ml), dried (MgSO₄), and freed of solvent in vacuo leaving the title product.

EXAMPLES 29 to 64

Following the procedures outlined in the specification and described in the above working Examples, the following compounds may be prepared.

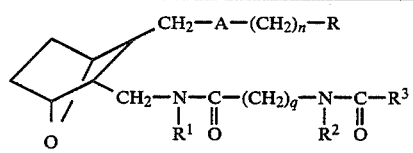

| Ex. No. | A | $(CH_2)_n$ | R | $R^1$ | $(CH_2)_q$ | $R^2$ | $R^3$ |
|---|---|---|---|---|---|---|---|
| 29. | CH=CH | −CH(CH₃)− | O=CN−OCH₃ | H | −(CH₂)₇H− | OH | −CH₂−C(H)=C(H)−CH₃− |
| 30. | (CH₂)₂ | −C(CH₃)(CH₃)− | O=CN(CH₃)−OC₂H₅ | H | −CH(CH₃)− | OH | C₆H₅ |
| 31. | (CH₂)₂ | (CH₂)₄ | O=CNHC₆H₅ | OH | −CH₂− | H | C₆H₅ |

-continued

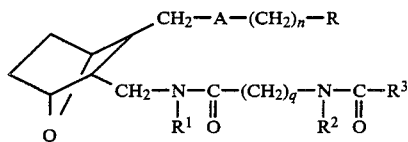

| Ex. No. | A | $(CH_2)_n$ | R | $R^1$ | $(CH_2)_q$ | $R^2$ | $R^3$ |
|---|---|---|---|---|---|---|---|
| 32. | CH=CH | $-\underset{\underset{CH_2-}{\|}}{\overset{CH_3}{C}}-CH_3$ | $CO_2Li$ | OH | $-CH_2-\underset{CH_3}{\overset{\|}{CH}}-$ | H | $CH_2C_6H_5$ |
| 33. | CH=CH | $-\underset{CH_3}{\overset{\|}{CH}}-\underset{CH_3}{\overset{\|}{CH}}-$ | $CO_2Na$ | OH | $-CH_2-\underset{\underset{CH_3}{\|}}{\overset{CH_3}{C}}-$ | H | $-(CH_2)_2C_6H_5$ |
| 34. | $(CH_2)_2$ | $-\underset{F}{\overset{CH_3}{\underset{\|}{C}}}-CH_2-$ | $CO_2$glucamine salt | OH | $-CH_2-\underset{CH_3}{\overset{\|}{CH}}-CH_2-$ | H | $-C_6H_4-p-CH_3$ |
| 35. | CH=CH | $-\underset{F}{\overset{F}{\underset{\|}{CH}}}-\underset{}{\overset{\|}{CH}}-$ | $CO_2$tris salt | H | $-(CH_2)_3-$ | OH | $-C_6H_4-p-OH$ |
| 36. | $(CH_2)_2$ | $-\underset{F}{\overset{F}{C}}-CH_2-$ | $CH_2OH$ | H | $-CH_2-\underset{C_2H_5}{\overset{\|}{CH}}-$ | OH | $-OCH_2C_6C_5$ |
| 37. | $(CH_2)_2$ | $-(CH_2)_5$ | ![tetrazole] | H | $-CH_2-\underset{H}{\overset{CH_3}{\underset{\|}{C}}}-CH_2-$ | OH | $-SC_2H_5$ |
| 38. | CH=CH | $-CH_2-\underset{CH_3}{\overset{\|}{CH}}-CH_2-$ | $\overset{O}{\overset{\|}{C}}NH_2$ | OH | $-\underset{\underset{CH_3}{\|}}{\overset{CH_3}{C}}-CH_2-$ | H | $-OC_6H_5$ |
| 39. | $(CH_2)_2$ | $-CH_2-\underset{CH_3}{\overset{CH_3}{\underset{\|}{C}}}-$ | $\overset{O}{\overset{\|}{C}}\underset{H}{NOH}$ | OH | $(CH_2)_2$ | H | $-NH_2$ |
| 40. | CH=CH | $CH_2$ | $\overset{O}{\overset{\|}{C}}N(CH_3)_2$ | OH | $-CH_2-$ | H | $-NHCH_3$ |
| 41. | $(CH_2)_2$ | $(CH_2)_2$ | $\overset{O}{\overset{\|}{C}}\underset{OH}{N-CH_3}$ | H | $-CH_2-\underset{CH_3}{\overset{CH_3}{\underset{\|}{C}}}-$ | OH | $-NHC_6H_5$ |
| 42. | CH=CH | $(CH_2)_3$ | $CO_2H$ | H | $-CH_2-\underset{CH_3}{\overset{\|}{CH}}-\underset{CH_3}{\overset{\|}{CH}}-CH_2-$ | OH | $NCH_3(C_2H_5)$ |
| 43. | $(CH_2)_2$ | $(CH_2)_4$ | $CH_2OH$ | OH | $(CH_2)_2$ | H | $-N(CH_3)_2$ |
| 44. | CH=CH | $-CH_2\underset{F}{\overset{F}{C}}-$ | ![tetrazole] | H | $(CH_2)_3$ | OH | H |
| 45. | $(CH_2)_2$ | $-CH_2-\underset{CH_3}{\overset{CH_3}{\underset{\|}{C}}}-$ | $\overset{O}{\overset{\|}{C}}N(C_2H_5)_2$ | OH | $-\underset{F}{\overset{\|}{CH}}-CH_2-$ | H | $-NH-CH_2-C_6H_5$ |
| 46. | CH=CH | $(CH_2)_5$ | $\overset{O}{\overset{\|}{C}}NHC_6H_5$ | H | $-\underset{F}{\overset{F}{C}}-CH_2$ | OH | $-(CH_2)_2CH=CHCH_3$ |

-continued

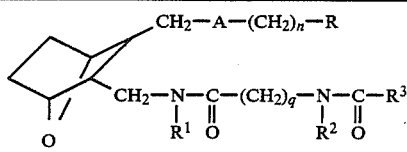

| Ex. No. | A | $(CH_2)_n$ | R | $R^1$ | $(CH_2)_q$ | $R^2$ | $R^3$ |
|---|---|---|---|---|---|---|---|
| 47. | $(CH_2)_2$ | $-CH(CH_3)-CH(F)-$ | $CH_2OH$ | OH | $(CH_2)_2$ | H | $C_6H_5$ |
| 48. | $(CH_2)_2$ | $(CH_2)_2$ | tetrazolyl | OH | $CH_2$ | H | $-CH_2C_6H_5$ |
| 49. | CH=CH | $(CH_2)_3$ | $CO_2CH_3$ | H | $(CH_2)_3$ | OH | $-SC_4H_9$ |
| 50. | $(CH_2)_2$ | $(CH_2)_4$ | $CO_2CH_3$ | OH | $(CH_2)_8$ | H | $-SC_6H_5$ |
| 51. | CH=CH | $(CH_2)_5$ | $CO_2H$ | OH | $(CH_2)_{10}$ | H | $-NCH_3(C_6H_5)$ |
| 52. | CH=CH | $CH_2$ | $CO_2H$ | H | $(CH_2)_2$ | OH | H |
| 53. | $(CH_2)_2$ | $(CH_2)_2$ | $CH_2OH$ | OH | $(CH_2)_3$ | H | $CH_3$ |
| 54. | CH=CH | $(CH_2)_3$ | tetrazolyl | H | $(CH_2)_4$ | OH | $-CH=CH-CH_3$ |
| 55. | $(CH_2)_2$ | $(CH_2)_4$ | $-CN(CH_3)C_2H_5$ (C=O) | H | $(CH_2)_5$ | OH | $-C\equiv C-CH_3$ |
| 56. | CH=CH | $(CH_2)_5$ | $-CN(OH)(CH_3)$ (C=O) | OH | $(CH_2)_6$ | H | $-CH_2-C\equiv C-CH_3$ |
| 57. | CH=CH | $(CH_2)_3$ | $CO_2H$ | H | $CH_2$ | OH | $-SC_6H_5$ |
| 58. | CH=CH | $CH_2$ | $CO_2H$ | OH | $CH_2$ | H | $-CH_2-SC_2H_5$ (C=O) |
| 59. | $(CH_2)_2$ | $(CH_2)_3$ | $CH_2OH$ | H | $(CH_2)_2$ | OH | $-CH_2-SCH_2C_6H_5$ (C=O) |
| 60. | CH=CH | $(CH_2)_3$ | $CO_2H$ | H | $(CH_2)_3$ | OH | $-CH_2-S-C_2H_5$ |
| 61. | $(CH_2)_2$ | $(CH_2)_3$ | $-CNH_2O$ | OH | $CH_2$ | H | $-CH_2-S-CH_2-C_6H_5$ |
| 62. | CH=CH | $(CH_2)_3$ | $CO_2H$ | H | $CH_2$ | OH | $-CH_2-O-CH_2-C_6H_5$ |
| 63. | CH=CH | $CH_2$ | $CO_2H$ | OH | $CH_2$ | H | $-CH_2-NH-CH_2C_6H_5$ |
| 64. | $(CH_2)_2$ | $(CH_2)_3$ | $CO_2CH_3$ | H | $(CH_2)_2$ | OH | $-CH_2-S-C_4H_9$ |

What is claimed is:

1. A compound having the structure

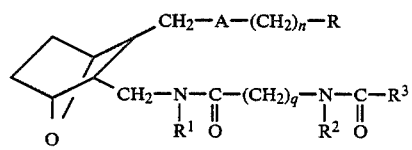

including all stereoisomers thereof, wherein A is —CH=CH— or —CH$_2$—CH$_2$—; n is 1 to 5; R is $CO_2H$, $CO_2$alkyl, $CO_2$ alkali metal, $CO_2$ polyhydroxyamine salt, —CH$_2$OH,

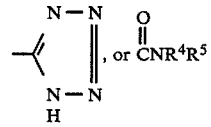, or $CNR^4R^5$ (C=O)

wherein $R^4$ and $R^5$ are the same or different and are H, lower alkyl, hydroxy, lower alkoxy or aryl at least one of $R^4$ and $R^5$ being other than hydroxy and lower alkoxy; q is 1 to 12; $R^1$ is H or OH; $R^2$ is OH or H provided that one of $R^1$ and $R^2$ is OH and the other is H; and $R^3$ is H, lower alkyl, lower alkenyl, lower alkynyl, aryl, arylalkyl, lower alkoxy, arylalkoxy, aryloxy, alkylamino, arylamino, arylalkylamino, lower alkyl-S-, aryl-S-, arylalkyl-S-,

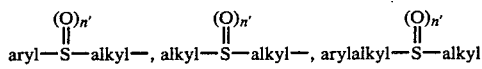

(wherein n' is 0, 1 or 2), alkylaminoalkyl, arylaminoalkyl, arylalkylaminoalkyl, alkoxyalkyl, aryloxyalkyl or arylalkoxyalkyl, wherein lower alkyl or alkyl alone or as part of another group contains 1 to 12 carbons and is unsubstituted or is substituted with halo, $CF_3$, alkoxy, aryl, alkyl-aryl, haloaryl, cycloalkyl, alkylcycloalkyl, hydroxy, alkylamino, alkanoylamino, arylcarbonylamino, nitro, cyano, thiol or alkylthio;

cycloalkyl alone or as part of another group is a saturated cyclic hydrocarbon group containing 3 to 12 carbons, which is unsubstituted or substituted with 1 or 2 halogens, 1 or 2 lower alkyl groups, 1 or 2 lower alkoxy groups, 1 or 2 hydroxy groups, 1 or 2 alkylamino groups, 1 or 2 alkanoylamino groups, 1 or 2 arylocarbonyl amino groups, 1 or 2 amino groups, 1 or 2 nitro groups, 1 or 2 cyano groups, 1 or 2 thiol groups and/or 1 or 2 alkylthio groups; and aryl alone or as part of another group is a monocyclic or bicyclic aromatic group containing from 6 to 10 carbons in the ring portion and which is unsubstituted or is substituted with 1 or 2 lower alkyl groups, 1 or 2 halogens, 1 or 2 lower alkoxy groups, 1 or 2 hydroxy groups, 1 or 2 alkylamino groups, 1 or 2 alkanoylamino groups, 1 or 2 arylcarbonylamino groups, 1 or 2 amino groups, 1 or 2 nitro groups, 1 or 2 cyano groups, 1 or 2 thiol groups and/or 1 or 2 alkylthio groups.

2. The compound as defined in claim 1 wherein $R^1$ is OH and $R^2$ is H.

3. The compound as defined in claim 1 wherein $R^1$ is H and $R^2$ is OH.

4. The compound as defined in claim 1 wherein $R^3$ is alkyl, alkoxy or arylthioalkyl.

5. The compound as defined in claim 1 wherein A is CH=CH.

6. The compound as defined in claim 1 wherein n is 1 to 4.

7. The compound as defined in claim 1 wherein R is $CO_2$ alkyl or $CO_2H$.

8. The compound as defined in claim 1 having the name [1S-[1α,2β(5Z),3β,4α]]-7-[3-[[[[hydroxy(1-oxohexyl)amino]acetyl]amino]methyl]-7-oxabicyclo[2.2.1]hept-2-yl]-5-heptenoic acid or esters thereof, including all stereoisomers thereof.

9. The compound as defined in claim 1 having the name [1S-[1α,2β(5Z),3β,4α]]-7-[3-[[hydroxy[[1-oxoheptyl)amino]acetyl]amino]methyl]-7-oxabicyclo[2.2.1]hept-2-yl]-5-heptenoic acid or esters thereof, including all stereoisomers thereof.

10. A method of inhibiting platelet aggregation and/or bronchoconstriction, which comprises administering to the circulatory system of a mammalian host an effective amount of a compound as defined in claim 1 or a pharmaceutically acceptable salt thereof.

11. The method as defined in claim 10 wherein said compound is administered in an amount within the range of from about 1 to about 100 mg/kg.

12. A composition for inhibiting platelet aggregation and/or bronchoconstriction comprising an effective amount of a compound as defined in claim 1 or a pharmaceutically acceptable salt thereof, and a pharmaceutically acceptable carrier therefor.

13. A method of treating peripheral vascular diseases, which comprises topically or systemically administering to a mammalian host an effective amount of a compound as defined in claim 1 or a pharmaceutically acceptable salt thereof.

* * * * *